US006477416B1

(12) United States Patent
Florio et al.

(10) Patent No.: US 6,477,416 B1
(45) Date of Patent: Nov. 5, 2002

(54) SYSTEM AND METHOD FOR AUTOMATICALLY AND ADAPTIVELY SEGMENTING AN ATRIAL BLANKING PERIOD

(75) Inventors: Joseph J. Florio, La Canada; Laurence S. Sloman, West Hollywood, both of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/572,488

(22) Filed: May 15, 2000

(51) Int. Cl.[7] .................................................. A61N 1/18
(52) U.S. Cl. ......................................................... 607/9
(58) Field of Search ................................ 600/509, 515, 600/521; 607/4, 5, 9, 28

(56) References Cited

U.S. PATENT DOCUMENTS

| | | | |
|---|---|---|---|
| 4,485,818 A | 12/1984 | Leckrone et al. | 128/419 PG |
| 4,624,260 A | 11/1986 | Baker | 128/419 PG |
| 4,712,555 A | 12/1987 | Thornander et al. | 128/419 PG |
| 4,722,341 A | 2/1988 | Hedberg et al. | 128/419 PG |
| 4,940,052 A | 7/1990 | Mann et al. | 128/419 PG |
| 4,944,298 A | 7/1990 | Sholder | 128/419 PG |
| 5,247,929 A | 9/1993 | Stoop et al. | 128/419 PG |
| 5,282,465 A | 2/1994 | van derVeen et al. | 128/419 PG |
| 5,470,342 A | 11/1995 | Mann et al. | 607/5 |
| 5,549,649 A | 8/1996 | Florio et al. | 607/15 |
| 5,591,214 A * | 1/1997 | Lu | 607/9 |
| 5,609,610 A | 3/1997 | Nappholz | 607/9 |
| 5,776,167 A * | 7/1998 | Levine et al. | 607/9 |
| 5,788,717 A | 8/1998 | Mann et al. | 607/14 |
| 6,101,416 A * | 8/2000 | Sloman | 607/28 |

OTHER PUBLICATIONS

Levine, Paul A., M.D., FACC, "The Importance of the Post–Ventricular Atrial Blanking Period (PVAB) with Respect to Far Field R Wave Detection", St. Jude Medical CRMD, pp 1–16 (Nov. 22, 1999).

* cited by examiner

Primary Examiner—Jeffrey R. Jastrzab
Assistant Examiner—Frances P. Oropeza

(57) ABSTRACT

An implantable stimulation device delivers a stimulation pulse in the ventricular chamber of a patient's heart and automatically adjusts a post-ventricular atrial blanking period. The stimulation device generates a ventricular stimulation pulse to trigger an evoked response, in order to produce a ventricular far-field signal that follows a successfully captured ventricular stimulation pulse. The stimulation device further includes an atrial sense circuit that senses the ventricular far-field signal, and a control system that adaptively segments the post-ventricular atrial blanking period in a post-ventricular atrial blanking period (PVAB) which is fixed in duration, and a variable far-field interval (FFI) window. PVAB is initiated upon the delivery of the ventricular stimulation pulse, such that events sensed outside the segmented post-ventricular atrial blanking (SPVAB) period are presumed to be intrinsic atrial events, and events sensed within the far-field interval window are presumed to be far-field signals. The far-field interval window is preferably centered on a previously sensed far-field R-wave. If an intrinsic ventricular event is sensed, the stimulation device does not initiate the PVAB period but rather sets the FFI window.

33 Claims, 7 Drawing Sheets

SYSTEM AND METHOD FOR AUTOMATICALLY AND ADAPTIVELY SEGMENTING AN ATRIAL BLANKING PERIOD

FIELD OF THE INVENTION

The present invention relates in general to cardiac stimulation devices, such as pacemakers, defibrillators, cardioverters, implantable cardioverter-defibrillators ("ICDs"), and similar cardiac stimulation devices that are capable of monitoring and detecting electrical activities and events within the heart. In particular, this invention pertains to a system and method for optimizing the post-ventricular atrial blanking period of an atrial channel of an implantable dual chamber stimulation device, by implementing a segmented post-ventricular atrial blanking period and properly identifying far-field signals sensed on an atrial channel.

BACKGROUND OF THE INVENTION

Implantable medical devices, such as pacemakers, defibrillators, cardioverters, and implantable cardioverter-defibrillators ("ICDs"), collectively referred to herein as implantable cardiac stimulating devices, are designed to monitor and stimulate the heart of a patient who suffers from a cardiac arrhythmia. Using leads connected to a patient's heart, these devices typically stimulate the cardiac muscles by delivering electrical pulses in response to measured cardiac events that are indicative of a cardiac arrhythmia. Properly administered therapeutic electrical pulses often successfully reestablish or maintain the heart's regular rhythm.

Implantable cardiac stimulating devices can treat a wide range of cardiac arrhythmias by using a series of adjustable parameters to alter the energy, shape, location, and frequency of the therapeutic pulses. The adjustable parameters are usually defined in a computer program stored in a memory of the implantable device. The program, which is responsible for the operation of the implantable device, can be defined or altered telemetrically by a medical practitioner using an external implantable device programmer.

Programmable pacemakers are generally of two types: (1) single-chamber pacemakers, and (2) dual-chamber pacemakers. In a single-chamber pacemaker, the pacemaker provides stimulation pulses to, and senses cardiac activity within, a single-chamber of the heart, either the right ventricle or the right atrium. In a dual-chamber pacemaker, the pacemaker provides stimulation pulses to, and senses cardiac activity within, two chambers of the heart, namely both the right atrium and the right ventricle. The left atrium and left ventricle can also be sensed and paced, provided that suitable electrical contacts are effected therewith.

One problem faced with the advent of dual-chamber pacemakers is that when a pacemaker delivers a stimulation pulse to the ventricle during an appropriate portion of a cardiac cycle, this pulse would be sensed by the atrial channel. Therefore, it is a common practice in the art to apply a post-ventricular atrial blanking (PVAB) period upon delivery of a ventricular stimulation pulse, in order to prevent the saturation of the sense amplifiers of the atrial channel. Because ventricular and atrial responses are sensed through the same lead electrodes through which the stimulation pulses are delivered, the resulting polarization signal, also referred to as an "afterpotential", formed at the electrodes, can corrupt the evoked response which is sensed by the sensing circuits. This undesirable situation occurs often because the polarization signal can be three or more orders of magnitude greater than the evoked response.

Furthermore, the lead polarization signal is not easily characterized; it is a complex function of the lead materials, lead geometry, tissue impedance, stimulation energy and other variables, many of which are continually changing over time. By disabling the atrial sense amplifier, that is applying a refractory or "blanking" period, upon the delivery of a ventricular stimulating pulse, the atrial sense amplifier is not affected by the ventricular stimulation pulse. At a specified time interval after the delivery of a ventricular stimulating pulse, the atrial sense amplifiers are enabled again to sense intrinsic or evoked atrial events.

However, the PVAB period poses a new problem in that it may occur mid-way or even late in the atrial cycle and may therefore result in an atrial channel inability to sense the next intrinsic atrial event. Essentially, the atrial channel is "blinded" to rapid atrial rates precluding proper diagnostic and therapeutic measures by the implanted cardiac device. Instead, a missed atrial event would trigger an atrial stimulation pulse to be inappropriately delivered by the pacemaker. Such inappropriate pacing could endanger the patient by inducing a sequence of events that might induce cardiac arrhythmias.

Another problem faced with the development of dual-chamber pacemakers is that the evoked R-wave (the electrical signal associated with ventricular contraction) subsequent to a ventricular stimulation pulse will typically propagate to the atrium in patients with intact atrioventricular ("AV") conduction. This propagated signal of a ventricular R-wave in the atria is commonly referred to as a "far-field R-wave" (FFR). Even a premature ventricular contraction (PVC), an arrhythmic event common in many patients requiring implantable cardiac devices, can propagate and produce a far-field signal on the atrial channel. Such far-field signals sensed by the atrial channel could be interpreted as atrial events. This erroneous sensing could easily be misinterpreted by the pacemaker's controlling operations as a change in atrial rate or even an atrial arrhythmia and consequently invoke improper therapeutic measures, potentially harming the patient.

In order to overcome this risk, the post-ventricular atrial blanking period employed upon the delivery of a ventricular pulse is commonly programmed long enough to encompass the far field signal associated with the propagation of a ventricular R-wave subsequent to a ventricular stimulation pulse. This post-ventricular atrial blanking period is commonly programmed to be a fixed time interval, typically 150 msec.

However, this relatively long, fixed post-ventricular atrial blanking period can exacerbate the limitations of a dual-chamber device in that the ability of the pacemaker to detect high atrial rates may be further impaired.

The window of time that the atrial channel is enabled for sensing atrial events is directly reduced as the post-ventricular atrial blanking period is lengthened to eliminate far-field signals from being sensed. Furthermore, conduction time between the ventricle and atrium will vary from patient to patient. In some patients, far field signals associated with ventricular events may occur even later than the typically programmed 150 msec blanking period. Using still longer blanking periods could more severely impair the pacemaker's ability to detect even normal atrial rates.

It would thus be desirable to provide a system and method for automatically adjusting the post ventricular atrial blanking period such that the blanking period following a ventricular stimulation pulse is minimized, thereby allowing the longest atrial sensing window possible in an implantable dual chamber stimulation device. Furthermore, it would be desirable to implement the system and method in a way that allows far-field signals sensed by the atrial channel to be properly interpreted as the ventricular events that they are associated with, thereby excluding them from atrial rate determinations. It would further be desirable to enable the pacemaker to perform this automatic post-ventricular atrial blanking period adjustment without requiring dedicated circuitry and/or special sensors.

SUMMARY OF THE INVENTION

The features of the present invention address the limitations and disadvantages discussed above. In accordance with the present invention, a system and method are provided for automatically adjusting the post-ventricular atrial blanking (PVAB) period of the atrial sensing channel of an implantable dual chamber stimulation device. The PVAB period will be segmented so as to maximize the atrial sensing window while eliminating the possibility of a far-field ventricular R-wave (FFR) from being detected on the atrial sense channel.

The system and method of the present invention overcome the limitations of atrial sensing associated with long refractory periods normally practiced in the art by providing for a considerably shortened blanking period upon delivery of a ventricular stimulation pulse followed by a far-field interval (FFI) window centered around a FFR signal. This method does not require special dedicated circuitry or special sensors to implement the automated procedure. All of the aforesaid advantages and features are achieved without incurring any significant disadvantage.

The present invention provides an implantable medical device, hereinafter referred to as pacemaker for simplicity purposes, which is equipped with cardiac data acquisition capabilities. A preferred embodiment of the pacemaker includes a control system for controlling the operation of the pacemaker, a set of leads for receiving atrial and ventricular signals and for delivering atrial and ventricular stimulation pulses, a set of sensing circuits comprised of sense amplifiers for sensing and amplifying the atrial and ventricular signals, a sampler, such as an A/D converter, for sampling atrial and/or ventricular signals, and a pulse generator for generating the atrial and ventricular stimulation pulses. In addition, the pacemaker includes memory for storing operational parameters for the control system, such as atrial or ventricular signal sampling parameters, and atrial or ventricular signal samples, and also includes a telemetry circuit for communicating with an external programmer.

In a preferred embodiment, the pacemaker control system sets a segmented post-ventricular atrial blanking (PVAB) period and automatically adjusts this segmented PVAB period as necessary. The segmented PVAB period includes two segments. The first segment is an absolute blanking period applied upon the delivery of a ventricular stimulation pulse, and the second segment is a far-field interval (FFI) window centered on a far field signal such as a FFR signal.

The first segment disables the atrial sense amplifier in the event of a ventricular pulse to avoid corruption of the atrial sense amplifier after ventricular pacing pulses. This period of "absolute blanking" in the present invention is considerably shorter than that practiced in the prior art. The possibility to shorten this absolute blanking period without posing undue risk to the patient is achieved by the implementation of the second segment of the PVAB period, i.e., the FFI window. If an event is detected outside the FFI window (i.e., an alert period), it is automatically presumed to be an atrial event (i.e., a P-wave).

During the FFI window, the atrial sense amplifier is enabled to sense, but any signal occurring during this FFI window is classified as a non-atrial event, i.e., a far-field wave (either a far-field R-wave or a far-field T-wave). Alternatively, any such event can be evaluated further by the pacemaker control system, in order to verify whether this signal is an actual atrial event or indeed a far-field wave. The temporal location and duration of the FFI window may be set manually by a medical practitioner, or automatically through a program stored in the pacemaker's memory.

In one embodiment of the invention, a signal occurring within the FFI window is verified as a far-field R-wave by comparing it to a signal recognition template automatically produced by the pacemaker. The pacemaker produces this template by delivering a ventricular stimulation pulse and then sampling a resulting far-field R-wave that is expected to follow a successfully captured ventricular stimulation pulse. By sampling and averaging several such FFR waves, a signal recognition template of a FFR signal is produced. A signal received by the atrial sensing channel during the FFI window can therefore be compared to the far-field signal recognition template. If the FFI signal approximately equals the template, the pacemaker operation recognizes the signal as a non-atrial event. If an intrinsic ventricular event is sensed, the stimulation device does not initiate the PVAB period but rather sets the FFI window.

The system and method of the present invention thus automatically set a segmented post-ventricular atrial blanking period, and when necessary, verifies if a sensed atrial signal is a far-field signal associated with a ventricular event. This is accomplished without requiring dedicated or special circuitry and/or sensors. The system and method allow reliable sensing of atrial events in dual-chamber pacemakers where after-potentials and far-field signals limit reliable detection of atrial rhythm. In addition, the system and method enable dual-chamber pacemakers capable of automatic mode-switching to automatically adapt the PVAB period to allow sensing and appropriate classification of far-field signals during automatic mode-switching.

BRIEF DESCRIPTION OF THE DRAWINGS

These and other features and advantages of the invention will now be described with reference to the drawings of a preferred embodiment, which is intended to illustrate and not to limit the invention, and in which like numerals refer to like parts throughout the disclosure, and wherein.

DETAILED DESCRIPTION OF THE INVENTION

Figure 1:
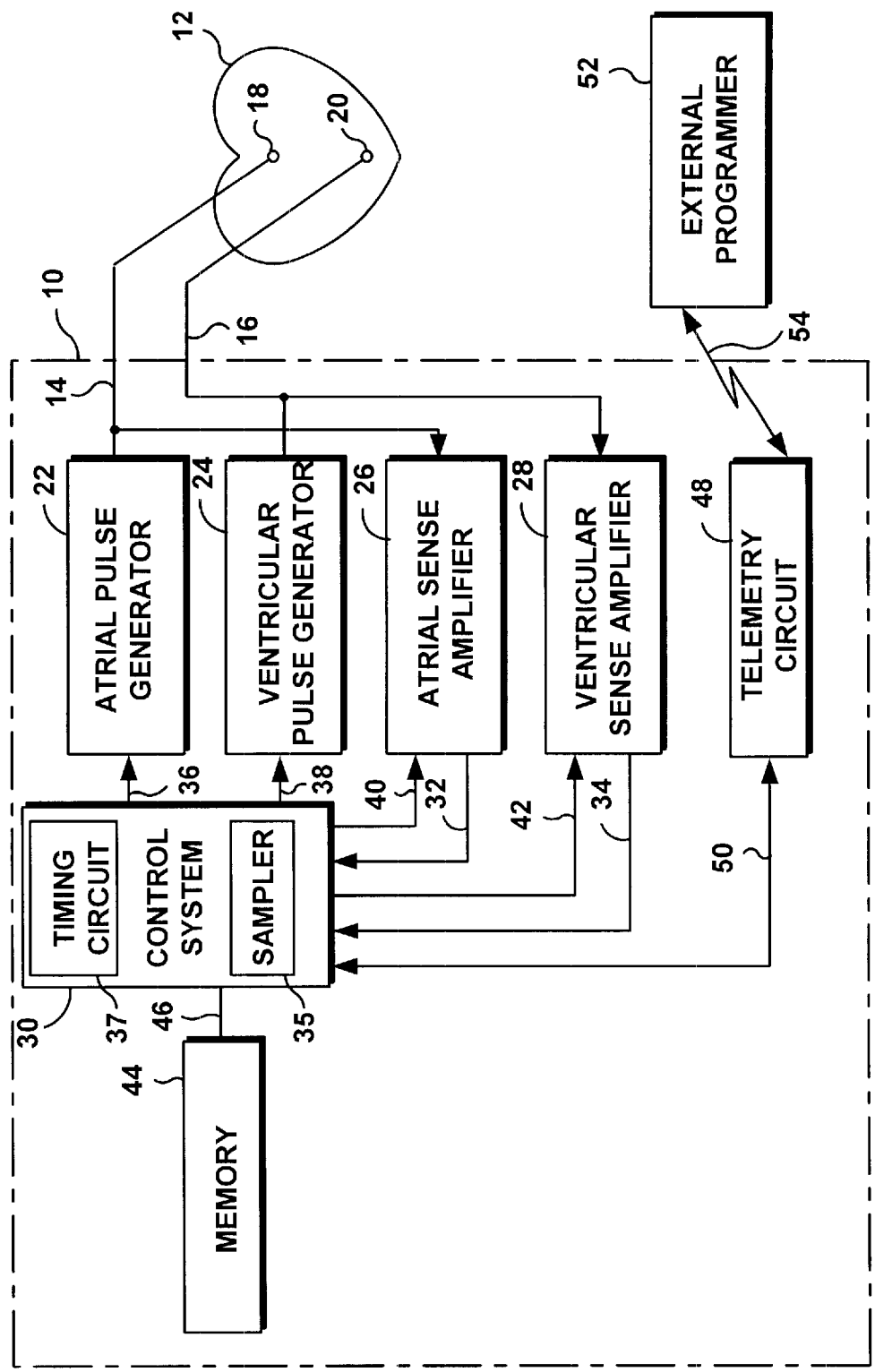
FIG. 1 is a block diagram of a dual-chamber pacemaker in accordance with the principles of the present invention.

With reference to FIG. 1, the system and method of the present invention are intended for use in an implantable cardiac stimulation device 10, such as a pacemaker, a defibrillator, a cardioverter, an implantable cardioverter-defibrillators ("ICDs"), or a similar stimulation device capable of monitoring and detecting electrical activities and events within a patient's organ such as a heart 12. For illustration purposes, the cardiac stimulation device will be described in term of a dual-chamber pacemaker which is programmed and implanted in a patient with intact atrio-ventricular ("AV") conduction.

The pacemaker 10 is coupled to a patient's heart 12 by way of leads 14 and 16. The lead 14 includes an electrode 18 which is in contact with one of the atria of the heart 12. The lead 16 includes an electrode 20 which is in contact with one of the ventricles. The lead 14 carries stimulating pulses to the electrode 18 from an atrial pulse generator 22, while the lead 16 carries stimulating pulses to the electrode 20 from a ventricular pulse generator 24. In addition, electrical signals from the atria are carried from the electrode 18, through the lead 14, to the input terminal of an atrial sense amplifier 26. Electrical signals from the ventricles are carried from the electrode 20, through the lead 16 to the input terminal of a ventricular sense amplifier 28.

Operatively controlling the dual-chamber pacemaker 10 is a control system 30. The control system 30 is preferably a microprocessor-based system such as for example that disclosed in commonly-assigned U.S. Pat. No. 4,940,052 of Mann, which is incorporated herein by reference in its entirety. The control system 30 may also be a state logic-based system such for example as that disclosed in commonly assigned U.S. Pat. No. 4,944,298 of Sholder, which is also incorporated herein by reference in its entirety. The control system 30 includes a timing circuit 37 comprised of a real-time clock, for providing timing functionality for monitoring cardiac events and for timing the application of therapeutic pulses by the pulse generators 22 and 24. The control system 30 also includes a sampler 35, such as an A/D converter, for generating digital signals representative of cardiac activity, by sampling the atrial and/or ventricular cardiac signals acquired by the respective amplifiers 26 and 28. Alternately, the sampler 35 may be implemented separately from the control system 30 and connected directly to the amplifiers 26 and 28.

The pacemaker 10 also includes a memory 44 which is coupled to the control system 30. The memory 44 allows certain control parameters used by the control system 30 in controlling the operation of the pacemaker 10 to be programmably stored and modified, as required, to customize the operation of the pacemaker 10 to suit the needs of a particular patient. In particular, parameters regulating the operation of the sampler 35 are stored in the memory 44. In addition, samples acquired by the sampler 35 may be stored in the memory 44 for later analysis by the control system 30.

The control system 30 receives the output signals from the atrial sense amplifier 26. Similarly, the control system 30 also receives the output signals from the ventricular sense amplifier 28. These various output signals are generated each time that an atrial event (e.g. a P-wave) or a ventricular event (e.g. an R-wave, a far-field R-wave ("FFR"), a far-field T-wave ("FFT"), or a far-field premature ventricular contraction (FFPVC) is sensed within the heart 12.

The control system 30 also generates an atrial trigger signal that is sent to the atrial pulse generator 22, and a ventricular trigger signal that is sent to the ventricular pulse generator 24. These trigger signals are generated each time that a stimulation pulse is to be generated by one of the pulse generators 22 or 24. The atrial stimulation pulse is referred to as the "A-pulse", and the ventricular stimulation pulse is referred to as the "V-pulse". The characteristics of these stimulation pulses are determined by pacing energy settings that are among the parameters stored in the memory 44.

A telemetry circuit 48 is further included in the pacemaker 10, and is connected to the control system 30. The telemetry circuit 48 may be selectively coupled to an external programmer 52 by means of an appropriate communication link 54, such as an electromagnetic telemetry link or a remote communication link such as a pair of modems interconnected via a telecommunications link and equipped with telemetry capabilities.

The operation of the pacemaker 10 is generally controlled by a control program stored in the memory 44 and executed by the control system 30. This control program is typically comprised of multiple integrated program modules, with each module bearing responsibility for controlling one or more functions of the pacemaker 10. For example, one program module may control the delivery of stimulating pulses to the heart 12, while another may control the verification of ventricular capture and ventricular pacing energy determination. In effect, each program module is a control program dedicated to a specific function or set of functions of the pacemaker 10.

Figure 2A:
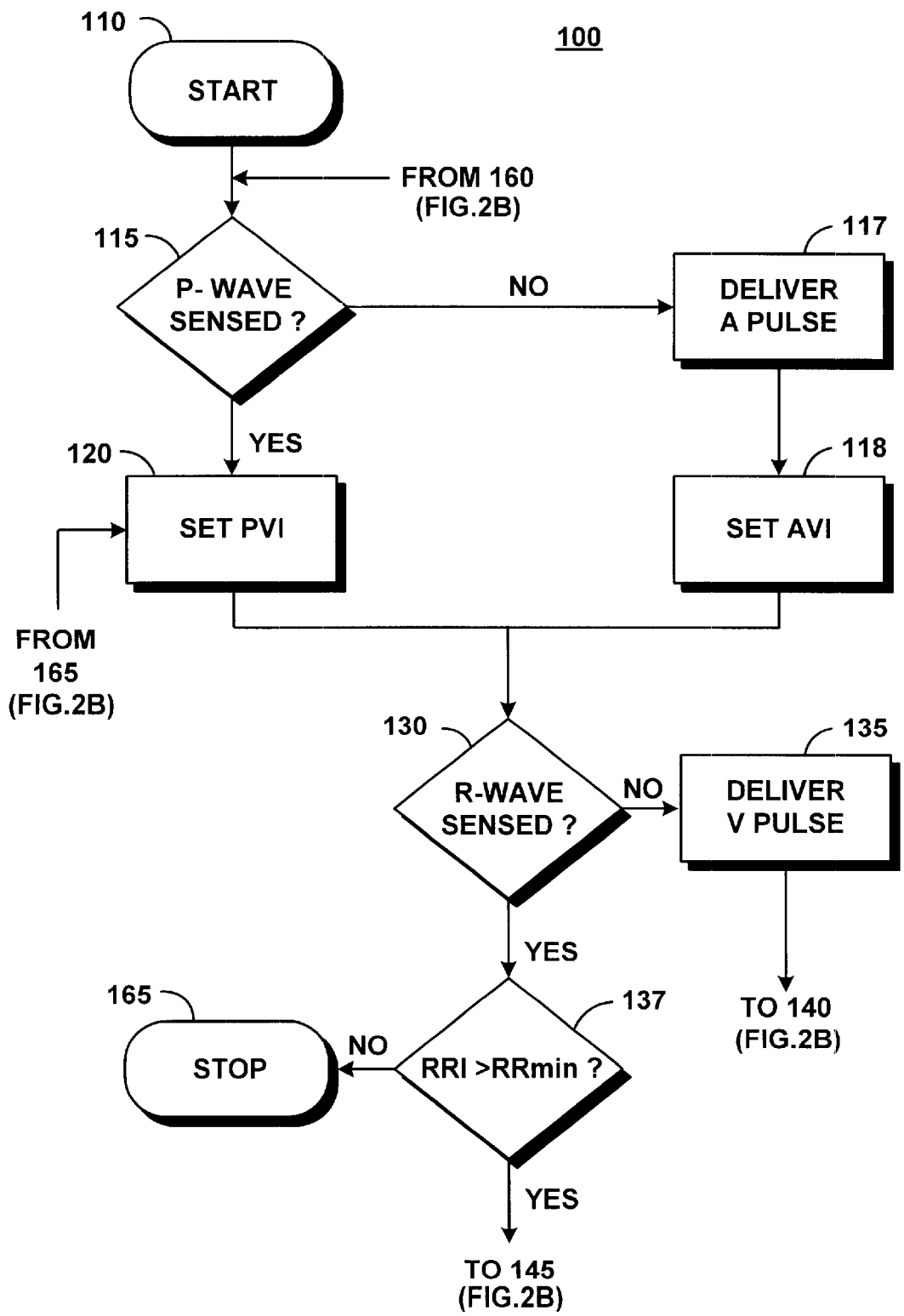
FIG. 2 is comprised of a FIG. 2A and FIG. 2B, and depicts a logic flow diagram of an automatic segmented post ventricular atrial blanking control program executed by a control system of the pacemaker of FIG. 1.
Figure 2B:
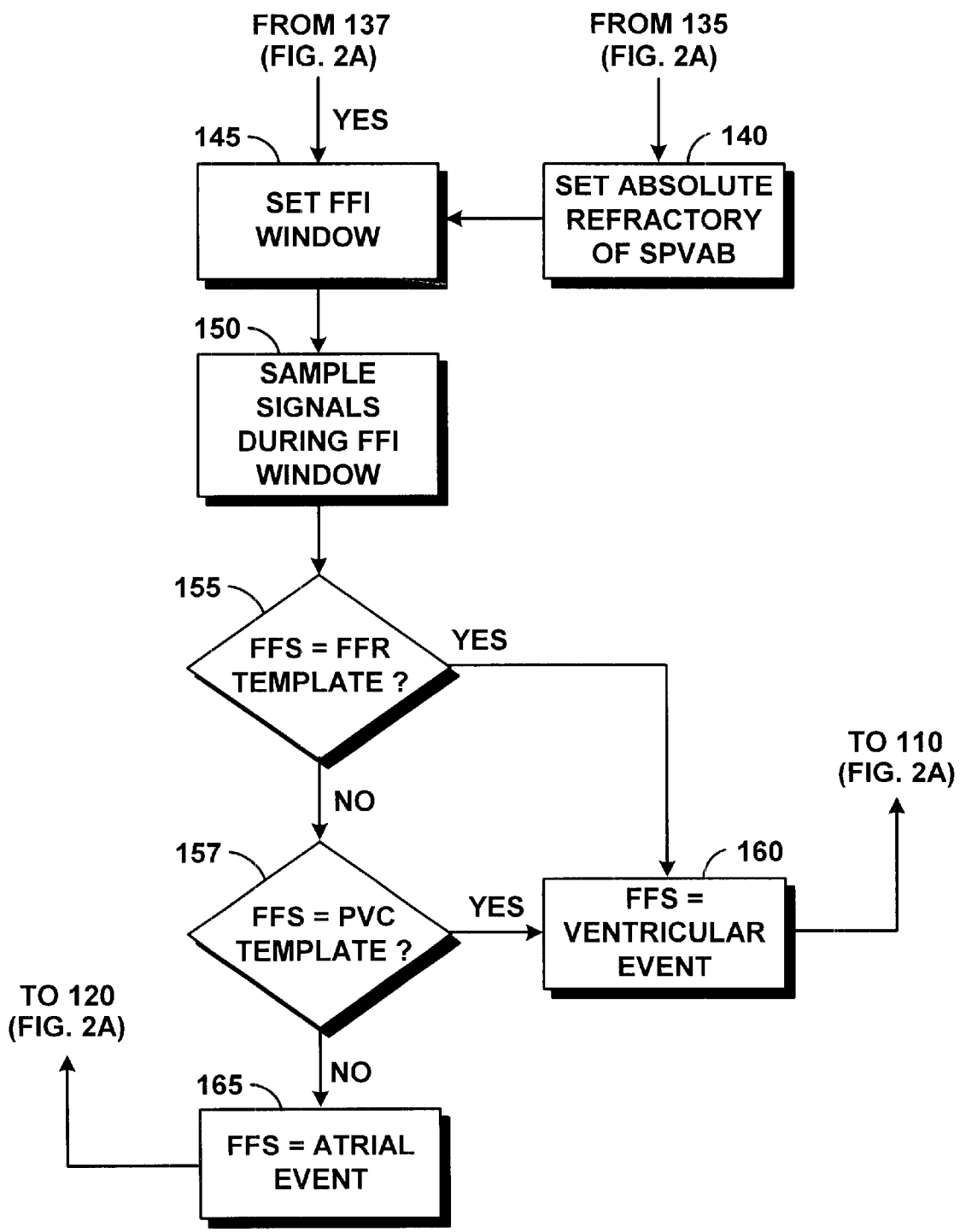

FIG. 2 is comprised of FIGS. 2A and 2B and depicts a logic flow diagram representing the operation of the control program for controlling a segmented post-ventricular atrial blanking period (SPVAB) of the atrial sense amplifier 26 executed by the control system 30 in accordance with the present invention. The control program will operate in such a way as to recognize different modes of operations of the pacemaker, preferably a mode-switching pacemaker, and apply the appropriate SPVAB period.

Figure 3:
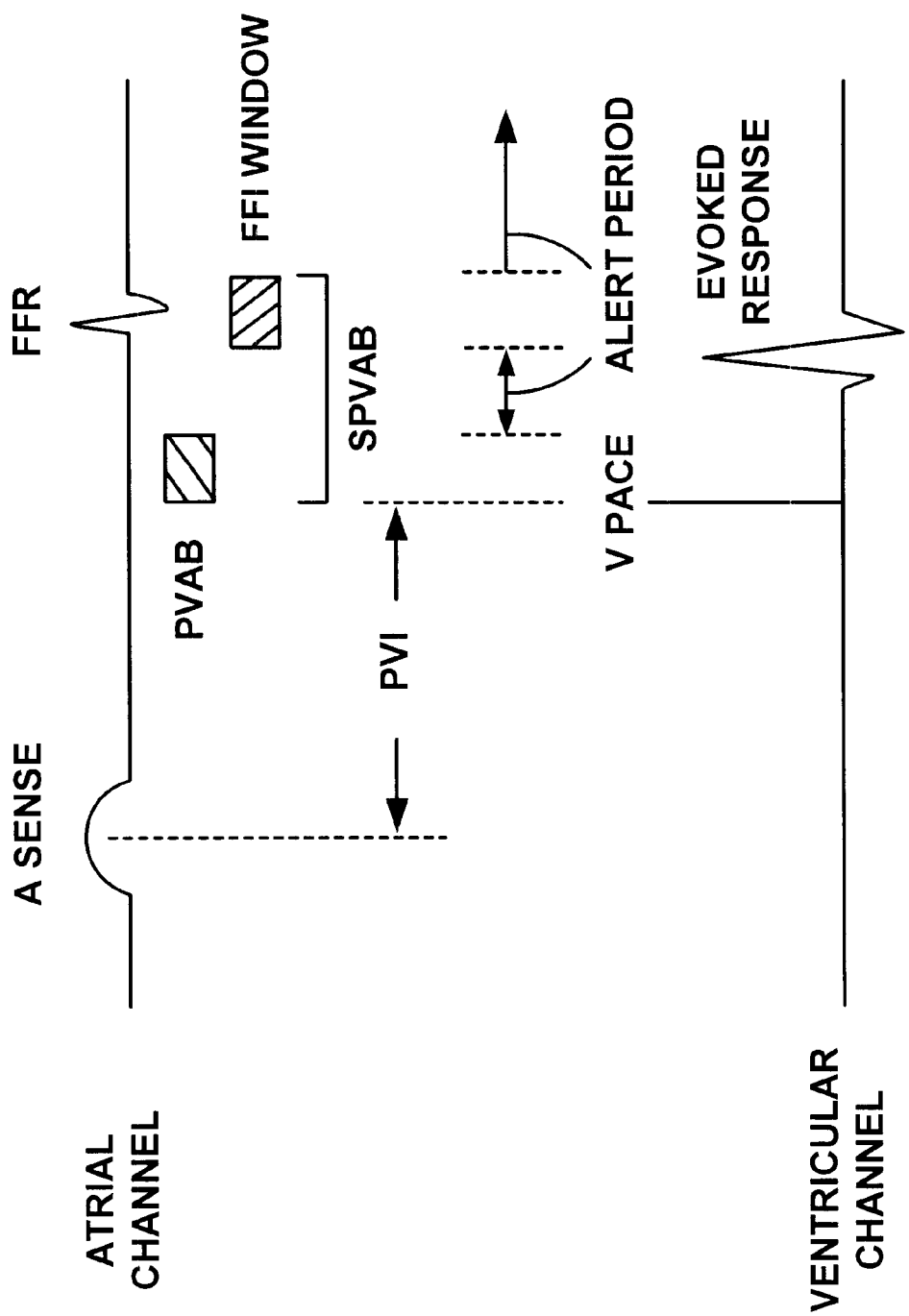
FIG. 3 is a timing diagram of an atrial channel and a ventricular channel illustrating the segmented post-ventricular atrial blanking process of FIG. 2 through the establishment of an absolute atrial blanking period and a far-field interval (FFI) window.

In the event of a paced ventricular pulse (V-pulse), the SPVAB period is segmented into two segments: a post-ventricular absolute blanking (PVAB) period generated upon the application of the V-pulse, and a far-field interval (FFI) window applied such that far-field signals received by the atrial sense amplifier that reflect the propagation of intrinsic R-waves, evoked R-waves, evoked T-waves, or premature ventricular contractions (PVCs) can be sensed and characterized as ventricular events and disregarded by atrial rate counting operations as non-atrial events. In this way, the invention optimizes the atrial sensing operation by preventing misinterpretation of far-field signals by the atrial channel, and further by minimizing atrial blanking periods, thus maximizing the window of time that the atrial channel is enabled to sense. The first segment, i.e., PVAB and the second segment, i.e., FFI window, are separated by an alert period (FIG. 3). The interval following the FFI window in the present cardiac cycle is also referred to as an alert period. An event occurring during these event periods is presumed to be an intrinsic atrial event.

FIG. 2 depicts a method 100 for setting the segmented PVAB period is illustrative of the operation of the present invention, and is implemented by the control system 30. The method 100 starts at step 110 and determines at step 115 if a P-wave is sensed. With further reference to FIG. 3, and following the sensing of an atrial event (P-wave) at step 115, the control system 30 sets a PV interval (PVI) at step 120.

If at step 115 a P-wave is not sensed, the control system 30 causes the atrial pulse generator 22 to deliver a stimulation pulse to the atrial chamber at step 117. The control system 30 sets an AV interval (AVI) at step 118 rather than a PVI. Both the AVI and the PVI are programmed by the physician and can typically range between 25 msec and 250 msec according to the particular patient's need.

Following either one of steps 118 or 120, the method 100 proceeds to decision step 130 where it inquires if a ventricular event (R-wave) is sensed. If no intrinsic R-wave is sensed, the control system 30 causes the ventricular pulse generator 22 to deliver a stimulation pulse (V pulse) to the ventricular chamber at step 135. The delivery of the V pulse at step 135 initiates a segmented PVAB (SPARB) period on the atrial channel at step 140 (FIG. 2B), as it is illustrated in FIG. 3. Following the V pulse, the absolute blanking period (PVAB) of the SPVAB period is triggered. This short PVAB period ranges between approximately 6 msec and 100 msec, and preferably ranges between approximately 6 msec and 60 msec. Typically, the PVAB is set to approximately 12 msec, and prevents the saturation of the atrial sense amplifier 26 resulting from the ventricular pulse. The PVAB period is preferably a programmable parameter.

The evoked ventricular response to the V pulse delivered at step 135 typically propagates to, and is sensed by, the atrial sense amplifier 26 through the atrial lead 14 as an atrial signal, or more specifically as a far-field signal. This far-field signal associated with the evoked R-wave is denoted by the designation FFR.

The method 100 then proceeds to step 145 (FIG. 2B) and sets a far-field interval (FFI) window based on the temporal location of FFR (FIG. 3). According to one embodiment, the FFI window is substantially centered on the sensed FFR.

The FFI window can be set in two ways: manually or automatically. A manual setting is accomplished by means of the external programmer 52. The user or physician visually identifies the FFR signal on a monitor incorporated with the external programmer, and adjusts the FFI window so that it is centered on the FFR signal. The duration of the FFI window, that is the time that the window extends on either side of the FFR signal is also programmed. A preferred duration of the FFI window is approximately 40 msec, that is ±20 msec around FFR. These programmed settings are stored in the memory 44, and are applied by the control system 30 during the operation of method 100. The FFI window duration ranges between approximately 10 msec and 300 msec, and is preferably about 40 msec.

Setting the FFI window automatically requires that the results of a previously determined average atrioventricular conduction time (CT) be invoked. Although one method for determining the average CT will be described in detail later in connection with FIG. 5, any method established in the field could alternatively be used for determining the average CT. Briefly, such a method entails: (1) verifying a stable ventricular rate; (2) measuring the interval between the intrinsic R-wave and a FFS following the intrinsic R-wave over a specified number of cardiac cycles, for example, eight to ten; (3) averaging these measured intervals; (4) determining if the average interval is within a given tolerance; and (5) if so, storing it in the memory 44 as the conduction time (CT) average. The FFI window is then set at step 145 such that it is automatically centered in time on the FFR, as determined by the temporal location of the intrinsic R-wave plus the CT average.

At step 145 the far-field interval (FFI) window is set based on manually programmed values or automatically determined CT intervals. The average CT interval for a ventricular event is determined as the interval from the V pulse event to the FFR signal, or the time from the evoked R-wave to the FFR signal. The FFI window is then automatically centered on the FFR as determined by the temporal location of the V pulse plus the CT average, or the evoked R-wave plus the CT average.

Figure 4:
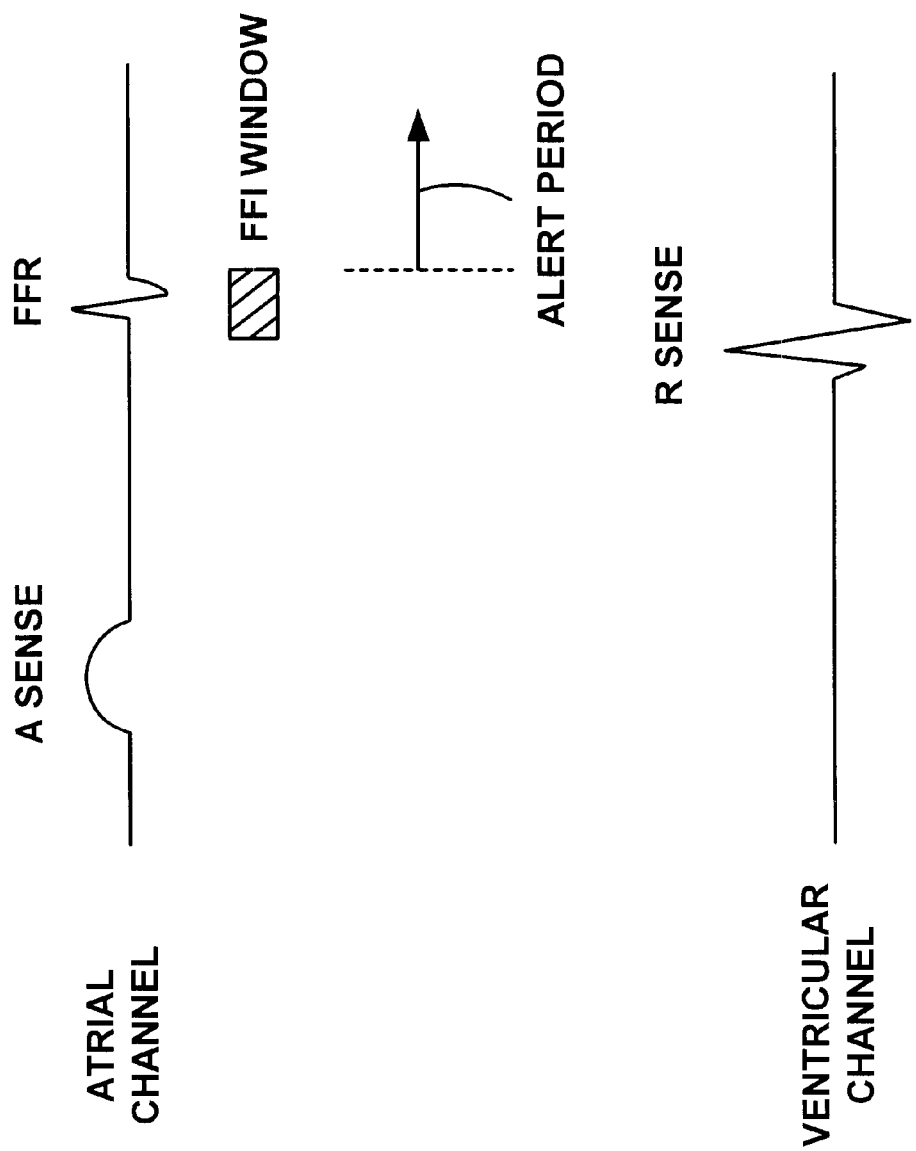
FIG. 4 is a timing diagram of the atrial channel and ventricular channel illustrating the establishment of a FFI window following a ventricular sensed event.

Returning now to step 130 and with further reference to FIG. 4, if an intrinsic R-wave is sensed, the time interval from the previously sensed R-wave to the newly sensed R-wave (RRI) is compared to a predetermined minimum R-to-R interval (RRmin) at decision step 137. If RRI is less than RRmin, this indicates an increase in the ventricular rate above a desired maximum value, and the adjustment of the SPVAB period is aborted at step 165. The RRmin is preferably programmed by the physician to reflect an increase, typically 20 beats per minute, above a programmed base rate. This feature is incorporated as a safety feature to prevent automatic adjustment of the PVAB period during periods of heart rate instability.

Typically, the intrinsic ventricular R-wave propagates to, and is sensed by, the atrial sense amplifier 26 through the atrial lead 14 as a far-field signal. This far-field signal associated with the R-wave is denoted by FFR. If at decision step 137 RRI is found to be greater than the RRmin, the method 100 proceeds to step 145 (FIG. 2B) and sets a far-field interval (FFI) window based on the temporal location of FFR. According to one embodiment, the FFI window is substantially centered on the sensed FFR. In this situation, the method 100 does not set an post-ventricular absolute blanking (PVAB) period as the concern about the atrial sense amplifier 26 saturating is significantly reduced. Because the PVAB period is now eliminated, the capability of the pacemaker 10 to unmask high rate atrial events is significantly improved.

Returning now to step 145, the far-field interval (FFI) window would again be set in the same way as described above, based on manually programmed values or automatically determined CT intervals. However, the average CT interval for a ventricular event is determined as the interval from the R sense event to the FFR signal. The FFI window is then automatically centered on the FFR as determined by the temporal location of the R sense event plus the CT average.

The sampler 35 of the control system 30 samples any signals sensed by the atrial sense amplifier 26 during the FFI window at step 150. In a preferred embodiment, any signal that occurs within the FFI window is not be used by the control system operation responsible for atrial rate determination, and is simply disregarded as a ventricular event. Alternatively, that signal could be further evaluated to ascertain that it is in fact a non-atrial event, such as a FFR signal. To this end, the control system 30 compares, at decision step 155, the sample signal obtained at step 150 with a far-field R-wave recognition template ("FFR template") stored in the memory 44, to determine whether the sample signal is approximately equal to the FFR template. The FFR template is preferably a representative morphology of a typical FFR that occurs in the patient's heart 12.

The FFR template, which might include signal amplitude and signal morphology characteristics, may be defined by the medical practitioner using the external programmer 52, or, preferably, it may be automatically determined by the control system 30. The control program module described below in connection with FIG. 5, demonstrates a technique for automatically determining the FFR template.

If the control system 30 determines at step 155 that the sample signal (or FFS) substantially matches the FFR template, then the sample signal is recognized at step 160 as a far field event, such as a far-field R-wave (FFR), and is disregarded as a non-atrial event by the operation of control system 30. The method 100 then returns to step 115 where it awaits for the next atrial event.

If the control system 30 determines at decision step 155 that the sample signal does not substantially match the FFR template, it will then proceed to decision step 157 where it compares the sample signal to a far-field premature ventricular contraction (FFPVC) recognition template stored in the memory 44. The FFPVC template is preferably a representative morphology of a typical premature ventricular contraction that occurs in the patient's heart 12. If the sample signal substantially matches the far-field PVC template, the FFS is recognized by the control system 30, at step 160, as a PVC signal, and is disregarded as a non-atrial event by the operations of control system 30. The method 100 then returns to step 115 and awaits for the next atrial event.

If the control system 30 determines at decision step 157 that the sample signal does not substantially match the FFPVC template, the control system 30 proceeds to step 165. Having eliminated the possibility (at steps 155 and 165) that the sample signal occurring within the FFI window is not associated with any ventricular event, the signal may then be interpreted, with a high level of confidence at step 165, as an atrial event. This sample signal is then used by the control system operation at step 120 to set the ventricular interval (PVI) and the steps discussed above are repeated. In this way, the atrial channel can detect a high atrial rate even when the P-wave occurs within the FFI window.

One purpose of the FFI window is thus to provide an opportunity for the control system 30 to sense a far-field signal and to correctly interpret it as a ventricular event rather than an atrial event. At the same time, the detection of a signal during the FFI window that is not associated with a far-field event can be correctly interpreted as an atrial event. In this way, only a very short absolute atrial blanking period is needed following a ventricular stimulation pulse. Thus, the total time that the atrial sense amplifier 26 is enabled is maximized improving its ability to detect rapid atrial rates. As stated earlier, the PVAB period in the current state of the art is set to a fixed amount of time, typically 150 msec or longer, to prevent the sensing of far-field signals. However, this limits the ability of the pacemaker to sense high trial rates because the atrial channel is completely "blinded" during the PVAB period. Furthermore, this fixed period does not solve the problem of late far-field R-waves that may occur, for example, as late as 180 msec following the application of a ventricular pulse. The present invention thus solves these problems by using the SPVAB period that includes a fixed PVAB and an adjustable FFI window.

Furthermore, the FFI window of the segmented PVAB period can be implemented not only for ventricular paced fixed events of the pacemaker operation, but also for all the event types of the pacemaker operation, including: atrial sensing/ventricular sensing (PR event); atrial sensing/ventricular pacing (PV event); atrial pacing/ventricular sensing (AR event); or atrial pacing/ventricular pacing (AV event). This allows correct for a interpretation of far-field signals occurring subsequent to intrinsic ventricular events and evoked events. It is thus one object of the invention that the control system 30 set the FFI window based on the event type and adjust the FFI window as necessary upon pacemaker automatic mode-switching. As indicated in the foregoing discussion related to FIG. 2, the FFI window position is based on a conduction time interval between a ventricular stimulation pulse and a FFR signal during ventricular pacing, which includes AV or PV modes of the pacemaker operation. However, during AR or PR modes of the pacemaker operation, the FFI window is positioned based on a conduction time interval between the intrinsic R-wave and a FFR.

Figure 5A:
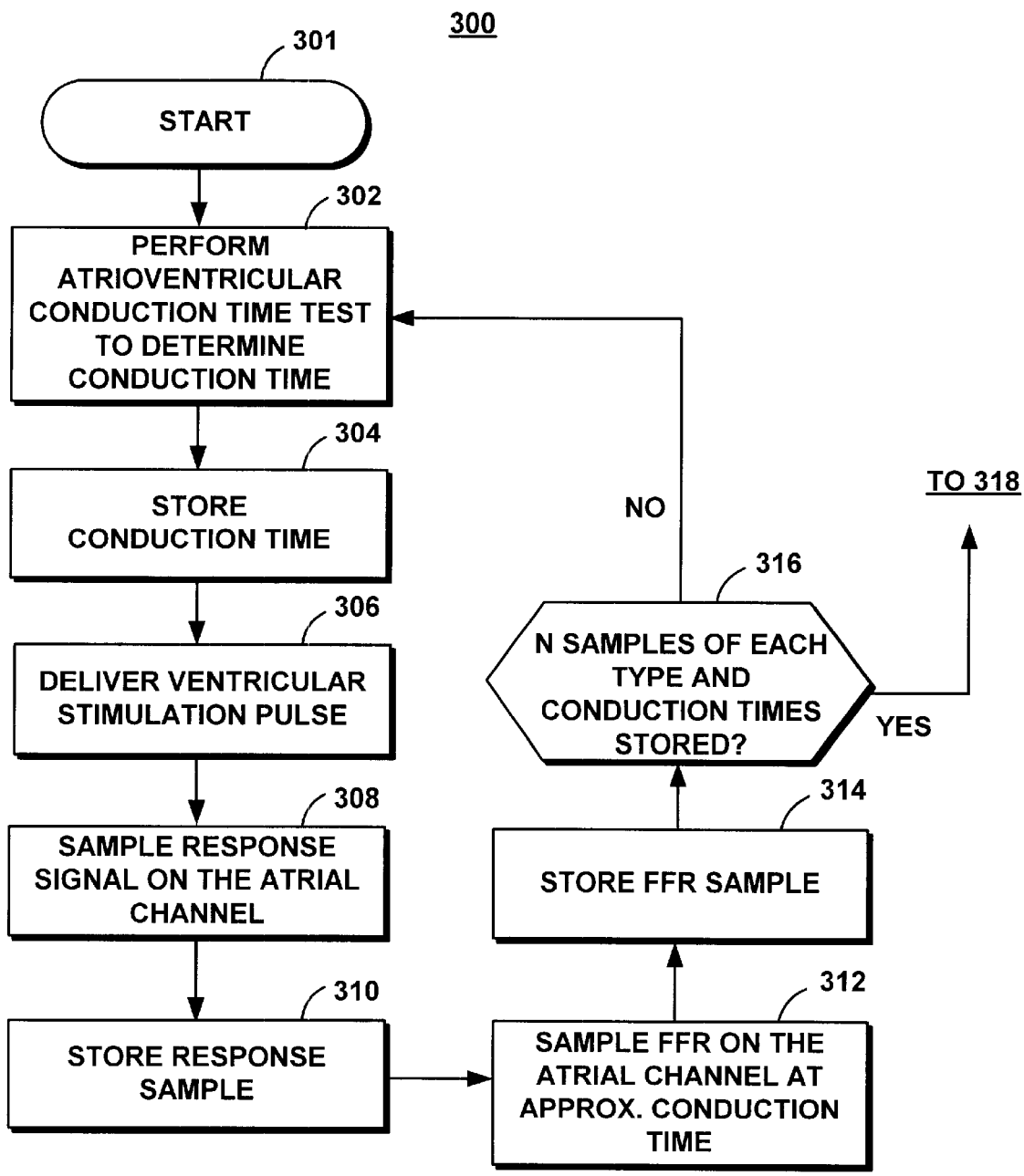
FIG. 5 is comprised of a FIG. 5A and FIG. 5B, and depicts a logic flow diagram of an automatic far-field signal recognition template determination program executed by the control system of the pacemaker of FIG. 1.
Figure 5B:
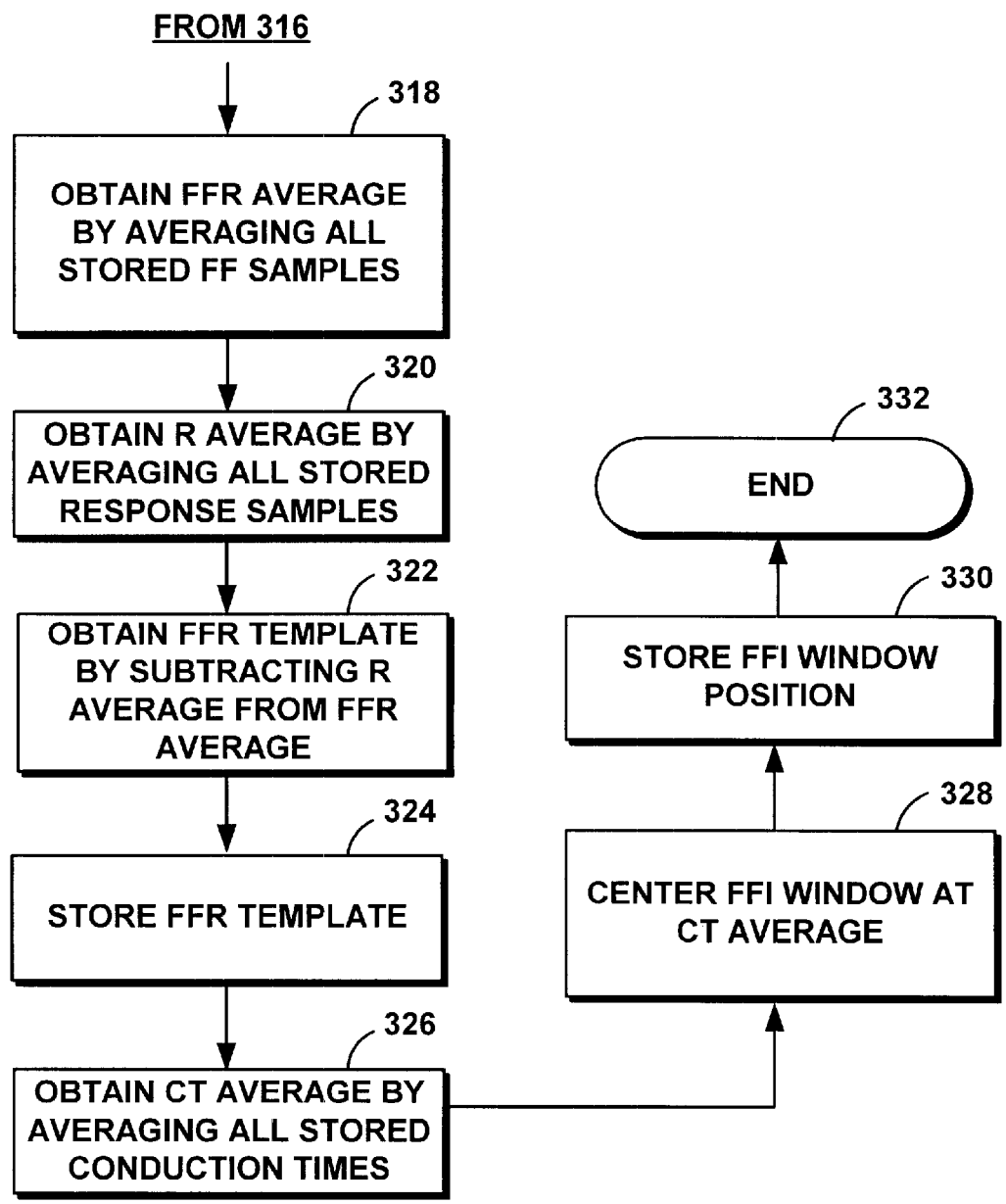

A method 300 will now be described by which far-field signal recognition templates are determined. FIG. 5 is comprised of FIGS. 5A and 5B, and depicts a logic flow diagram representing a preferred embodiment of a control program module within the control system 30, for automatically determining the FFR template. After the control program module begins at step 301 (FIG. 5A), the control system 30 performs an atrioventricular ("VA") conduction test at step 302, to determine the expected delay ("conduction time") between the delivery of the ventricular stimulation pulse and the sensing of the far-field R-wave signal by the atrial sense amplifier 26. The expected delay is equivalent to the VA conduction time. Various appropriate VA conduction time measurement procedures are well known in the art and will not therefore be described herein. At step 304, the control system 30 stores the conduction time determined at step 302 in the memory 44.

At step 306, the control system 30 causes the ventricular pulse generator 24 to deliver a stimulation pulse to the ventricular chamber of the heart 12. When delivered, the ventricular stimulation pulse triggers a ventricular pace response signal ("response signal") in the ventricular chamber that may include an evoked response representative of a ventricular contraction combined with a polarization signal. Typically, the ventricular stimulation pulse also triggers a subsequent ventricular contraction resulting in a ventricular R-wave evoked response that is sensed by the atrial sense amplifier 26 through the atrial lead 14 as a far-field R-wave (FFR).

At step 308 the control system 30 samples the response signal via the sampler 35, and at a step 310 stores the response sample signal in the memory 44. At step 312, the control system 30 samples the FFR signal via the sampler 35 after a predetermined delay following the delivery of the ventricular stimulation pulse at step 306, approximately equal to the VA conduction time determined at step 302. At step 314 the control system 30 stores the FFR signal sample signal in the memory 44.

At decision step 316 the control system 30 inquires whether a predetermined number (hereinafter "N") of each of the samples (steps 310 and 314), and conduction times (step 304) are stored in the memory 44. The parameter N may be selected by the medical practitioner using the programmer 52. In order to improve the accuracy of the FFR template, N should be set to a sufficient number of samples to accurately classify the conduction time (e.g., three samples or more).

If N conduction times, response sample signals, and FFR samples have not been stored, then the control system 30 returns from step 316 to step 302 to perform the VA conduction test. Thus, the control system 30 repeats steps 302 through 316 until N conduction times (step 304) and N sample signals of each sample signal type (steps 310, 314) have been stored in the memory 44.

When N conduction times and N sample signals of each sample signal type have been stored, then the control system 30 determines at step 318 (FIG. 5B) a FFR average representative of an average FFR sample signal by averaging all of the stored FFR sample signals (step 314, and optionally stores the FFR average in the memory 44. At step 320, the control system 30 similarly determines a R-average representative of an average response sample signal by averaging all of the stored response sample signals (step 310), and optionally stores the calculated R-average in the memory 44.

At step 322 the control system 30 determines the FFR template representative of a true far-field signal by subtracting R-average from FFR-average. Because the FFR-average represents the average far-field signal whereas the raw detected far-field signal may be mixed with the response signal, subtracting R-average which is representative of just the response signal including polarization and other noise from the FFR-average results in a representation of the true far-field R signal. At step 324 the FFR template is stored in the memory 44, so that it is available for future identification of a far-field signal during sampling of the FFI window of method 100 as described above in connection with FIGS. 2 and 3.

At step 326 the control system 30 determines an average expected delay value CT-average by averaging all the conduction times stored in the memory 44 and, at step 328, centers the FFI window at the CT-average. At step 330 the control system 30 stores the FFI window position to increase the capability of the atrial sense amplifier 26 to sense far-field signals, and then ends the control program module at step 332.

Likewise, a PVC signal recognition template could be generated by identifying PVCs when they occur, recording the response sample signal to memory 44, recording the far-field response to memory 44, measuring the conduction time between the PVC and its far-field signal, and averaging these signals to create a far-field PVC template in the control system 30.

While the invention described herein has been described with reference to specific embodiments, numerous modifications could be made thereto by those skilled in the art without departing from the scope of the invention.

What is claimed is:

1. A system for automatically adjusting a post-ventricular atrial blanking period in a stimulation device, comprising:
    a pulse generator for generating a ventricular stimulation pulse to trigger an evoked response so as to produce a corresponding atrial signal;
    an atrial sense circuit for sensing the atral signal;
    a control system connected to the pulse generator and the atrial sense circuit, for segmenting the post-ventrcular atrial blanking period into a first segment and a second segment, the first segment being initiated upon the delivery of the ventricular stimulation pulse, wherein events detected outside the first and second segments are identified as intrinsic atrial events; and
    wherein the second segment is timed relative to the ventricular stimulation pulse based on the atrial signal sensed by the atrial sense circuit.

2. The system according to claim 1, wherein the control system identifies events sensed within the second segment as far-field events.

3. The system according to claim 2, wherein the control system further identifies whether the far-field events are far-field R-waves.

4. The system according to claim 2, wherein the control system further identifies whether the far-field events are far-field T-waves.

5. The system according to claim 2, wherein the control system further identifies whether the far-field events are far-field premature ventricular contractions.

6. The system according to claim 1, wherein the control system identifies the second segment as a far-field interval window during which far-field ventricular events are sensed.

7. The system according to claim 6, wherein the control system disregards far-field ventricular events sensed during the far-field interval window.

8. The system according to claim 6, wherein the control system centers the far-field interval window on a previously sensed far-field R-wave.

9. The system according to claim 1, wherein the first and second segments are separated by an alert period; and
    wherein events sensed within the alert period are identified as intrinsic atrial events.

10. The system according to claim 1, wherein the system operates in one or more modes of operation; and
    wherein the control system sets a segmented post-ventrcular atrial blanking period based on event types occurring during the modes of operation.

11. The system according to claim 1, wherein the first segment is fixed in length.

12. The system according to claim 1, wherein the second segment is programmable.

13. The system according to claim 1, wherein the second segment is fixed in length.

14. The system according to claim 12, wherein the second segment-ranges between approximately 20 msec and 30 msec.

15. The system according to claim 14, wherein the far-field interval window duration is approximately 40 msec.

16. The system according to claim 12, wherein the first segment ranges between approximately 6 msec and 100 msec.

17. The system according to claim 12, wherein the first segment ranges between approximately 6 msec and 80 msec.

18. A simulation device that automatically adjusts a post-ventricular atrial blanking period, comprising:
    a pulse generator for generating a ventricular stimulation pulse to trigger an evoked response so as to produce an atrial signal;
    an atrial sense circuit for sensing the atrial signal; and
    a control system connected to the pulse generator and the atrial sense circuit for segmenting the post-ventricular atrial blanking period in a first segment and a second segment, the first segment being initiated upon delivery of the ventricular stimulation pulse, wherein events detected outside the first and second segments are identified as intrinsic atrial events; and
    wherein the first and second segments are temporally separated by an alert period.

19. A stimulation device for automatically adjusting a post-ventricular atrial blanking period, comprising:
    a ventricular sense circuit for sensing a ventricular event and for causing a far-field ventricular signal to be sensed on an atrial channel;
    an atrial sense circuit for sensing the far-field ventricular signal; and
    a control system connected to the ventricular sense circuit and the atrial sense circuit, for initiating a far-field interval window centered substantially about the far-field ventricular signal, wherein events detected outside the far-field interval window are identified as an intrinsic atrial event, and events detected within the far-field interval window are identified as non-atrial events.

20. The simulation device according to claim 19, wherein the control system identifies the non-atrial events as any one or more of: far-field R-waves, far-field T-waves, or far-field premature ventricular contractions.

21. The simulation device according to claim 19, wherein the control system centers the far-field interval window on a previously sensed far-field R-wave.

22. The simulation device according to claim 18, wherein the far-field interval window is any one of: fixed in length, programmable in length, or variable in length.

23. The simulation device according to claim 19, wherein the far-field interval window ranges between approximately 6 msec and 300 msec.

24. The simulation device according to claim 23, wherein the far-field interval window is approximately 40 msec.

25. A method for automatically adjusting a post-ventrcular atrial blanking period in a stimulation device, comprising;
   generating a ventricular stimulation pulse to trigger an evoked response so as to produce a corresponding atrial signal;
   sensing the atrial signal;
   segmenting the post-ventricular atrial blanking period in a first segment and a second segment;
   initiating the first segment upon the delivery of the ventricular stimulation pulse;
   initiating the second segment relative to a ventricular stimulation pulse at a time that is based upon the sensed atrial signal; and
   identifying events detected outside the first and second segments as intrinsic atrial events.

26. The method according to claim 25, further including identifying the second segment by setting a far-field interval window during which far-field ventricular events are sensed.

27. The method according to claim 26, further including identifying far-field events occurring within the far-field interval window as any one or more of: far-field R-waves, far-field T-waves, or far-field premature ventricular contractions.

28. The method according to claim 26, further including centering the far-field interval window on a previously sensed far-field R-wave.

29. The method according to claim 25, wherein segmenting the post-ventricular atrial blanking period includes setting the length of the first segment to any one of a fixed value or a programmable value.

30. The method according to claim 25, wherein segmenting the post-ventricular atrial blanking period indudes adaptively varying the length of the second segment.

31. The method according to claim 26, wherein identifying the second segment includes verifying if an event sensed within the far-field interval window is a far-field signal associated with a ventricular event.

32. A method for automatically adjusting a post-ventricular atrial blanking period in a stimulation device, comprising:
   sensing a ventricular event;
   sensing a far-field ventricular signal on an atrial channel;
   initiating a far-field interval window centered substantially about the far-field ventricular signal; and
   identifying events detected outside the far-field interval window as intrinsic atrial events, and events detected within the far-field interval window as non-atrial events.

33. A method for automatically adjusting a post-ventricular atrial blanking period in a stimulation device, comprising:
   generating a ventricular stimulation pulse to trigger a ventricular event and a corresponding far-field ventricular signal when ventricular stimulation is needed;
   sensing the ventricular event;
   sensing the far-field ventricular signal;
   if a ventricular stimulation pulse is generated:
      segmenting the post-ventricular atrial blanking period in a post-ventricular absolute refractory period and a far-field interval window;
      initiating the post-ventricular absolute refractory period upon the delivery of the ventricular stimulation pulse;
      initiating the far-field interval window at a time based on the sensed far-field ventricular signal; and
      identifying events detected outside the post-ventricular absolute refractory period and the far-field interval window as intrinsic atrial events; and
   if a ventricular event is sensed:
      initiating a far-field interval window; and
      identifying events detected outside the far-field interval window as intrinsic atrial events, and events detected within the far-field interval window as non-atrial events.

* * * * *